(12) United States Patent
Wu et al.

(10) Patent No.: US 9,627,633 B2
(45) Date of Patent: Apr. 18, 2017

(54) PERYLENE FUNCTIONALIZED PORPHYRIN DYES FOR DYE-SENSITIZED SOLAR CELLS

(71) Applicant: Agency for Science, Technology and Research, Singapore (SG)

(72) Inventors: Jishan Wu, Singapore (SG); Jie Luo, Singapore (SG); Changyun Jiang, Singapore (SG); Jie Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/903,585

(22) PCT Filed: Jul. 8, 2014

(86) PCT No.: PCT/SG2014/000323
§ 371 (c)(1),
(2) Date: Jan. 7, 2016

(87) PCT Pub. No.: WO2015/005869
PCT Pub. Date: Jan. 15, 2015

(65) Prior Publication Data
US 2017/0033302 A1    Feb. 2, 2017

(30) Foreign Application Priority Data
Jul. 8, 2013  (SG) ................. 201305268-3

(51) Int. Cl.
*H01L 51/50* (2006.01)
*H01G 9/20* (2006.01)
*C07F 3/06* (2006.01)
*C09B 47/00* (2006.01)
*H01L 51/00* (2006.01)

(52) U.S. Cl.
CPC ............ *H01L 51/0092* (2013.01); *C07F 3/06* (2013.01); *C09B 47/00* (2013.01); *H01G 9/2059* (2013.01)

(58) Field of Classification Search
CPC ....... H01L 51/0092; C07F 3/06; C09B 47/00; H01G 9/2059
USPC ........................................... 548/402
See application file for complete search history.

(56) References Cited

PUBLICATIONS

Written Opinion of the International Searching Authority for International Application No. PCT/SG2014/000323 dated Sep. 1, 2014, pp. 1-6.
International Preliminary Report on Patentability for International Application No. PCT/SG2014/000323 dated Jan. 21, 2016, pp. 1-8.
Yella et al., "Porphyrin-Sensitized Solar Cells with Cobalt (II/III)-Based Redox Electrolyte Exceed 12 Percent Efficiency," Science vol. 334, 2011, pp. 629-633.
Wang et al., "Enhance the Performance of Dye-Sensitized Solar Cells by Co-Grafting Amphiphilic Sensitizer and Hexadecylmalonic Acid on TiO2 Nanocrystals," Journal of Physical Chemistry B, vol. 107, 2003, pp. 14336-14341.
Lee et al., "Electronically Coupled Porphyrin-Arene Dyads for Dye-Sensitized Solar Cells," Dyes and Pigments, vol. 1, 2011, pp. 317-323.
Chen et al., "Porphyrin-Perylene Dyes for Dye-Sensitized Solar Cells," Journal of the Chinese Chemical Society, vol. 57, 2010, pp. 1141-1146.
Jiao et al, "Perylene Anhydride Fused Porphyrins as Near-Infrared Sensitizers for Dye-Sensitized Solar Cells," Organic Letter, vol. 13, No. 14, 2011, pp. 3652-3655.
Luo et al., "N-Annulated Perylene as an Efficient Electron Donor for Porphyrin-Based Dyes: Enhanced Light-Harvesting Ability and High-Efficiency Co(II/III)-Based Dye-Sensitized Solar Cells," Journal of American Chemical Society, vol. 136, No. 1, 2014, pp. 265-272.

*Primary Examiner* — Kristin Vajda
(74) *Attorney, Agent, or Firm* — Winstead, P.C.

(57) ABSTRACT

The invention relates to dyes for dye-sensitized solar cells, and in particular, to perylene functionalized porphyrin dyes for dye-sensitized solar cells. The invention further relates to a dye molecule comprising perylene functionalized porphyrin moiety.

23 Claims, 3 Drawing Sheets

PERYLENE FUNCTIONALIZED PORPHYRIN DYES FOR DYE-SENSITIZED SOLAR CELLS

CROSS-REFERENCE TO RELATED APPLICATION

This application claims the benefit of priority of Singapore Patent Application No. 201305268-3, filed Jul. 8, 2013, the contents of which being hereby incorporated by reference in its entirety for all purposes.

TECHNICAL FIELD

The invention relates to dyes for dye-sensitized solar cells, and in particular, to perylene functionalized porphyrin dyes for dye-sensitized solar cells. The invention further relates to a dye molecule comprising perylene functionalized porphyrin moiety.

BACKGROUND

Despite tremendous achievement in this area, dye-sensitized solar cells (DSSCs) suffer from some drawbacks which have prevented them from further commercialization. The major problems are low efficiency and stability. The highest efficiency reported until recently for DSSCs is 12.3%, which is around half as good as the best-known polycrystalline Si-cell (20.3%) and comparable to an amorphous Si-cell (9.5%). The efficiency of DSSC is mainly limited by the light absorption of the dyes and the interface charge separations between dyes and $TiO_2$ semiconductors. Hence, the key challenge to achieve high efficiency DSSCs is the development of suitable organic dyes that has extended light absorption spectrum in the near infrared range and could effectively generate electricity from light.

SUMMARY

Presently disclosed is a series of perylene functionalized porphyrin dyes for use in dye-sensitized solar cells (DSSCs). These dyes showed intense (molar extinction coefficient $>5 \times 10^4$ $M^{-1}$ $cm^{-1}$) and broad absorption in the visible and NIR range (350-900 nm). More than 11% power conversion efficiency has been achieved with the presently disclosed dyes and this is very close to the world record of 12.3% (Yella et al. Science 2011, 334, 629). Both the perylene moiety and porphyrin core have been found to be very important for their good performance in DSSCs.

Thus, in one aspect of the invention, there is provided a dye-sensitized solar cell comprising a dye molecule of Formula (I):

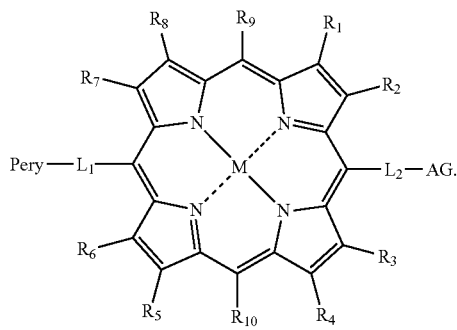

In Formula (I), M is zinc or cobalt. Alternatively, M may be, but not limited to, nickel, iron, and copper. Each of $L_1$ and $L_2$ is a linker and may be independently selected from the group consisting of a direct bond and an ethynylene group. Each of $R_1$, $R_2$, $R_3$, $R_4$, $R_5$, $R_6$, $R_7$, $R_8$ may be independently selected from the group consisting of hydrogen, halogen, $C_{1-30}$ alkyl, and $C_6$-$C_{20}$ aryl. Each of $R_9$ and $R_{10}$ may be independently a substituted or unsubstituted phenyl, or a substituted or unsubstituted benzyl. AG is an anchor group for attachment to a substrate.

In Formula (I), Pery is a perylene-based moiety of Formula (II):

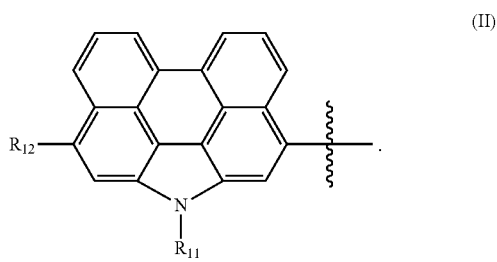

In Formula (II), each of $R_{11}$ and $R_{12}$ may be independently a substituted or unsubstituted phenyl, or a substituted or unsubstituted benzyl.

In another aspect of the invention, a dye molecule of Formula (I) is disclosed. The dye molecule may be employed as light harvesting dyes and employed in photocatalysis.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

Figure 1:
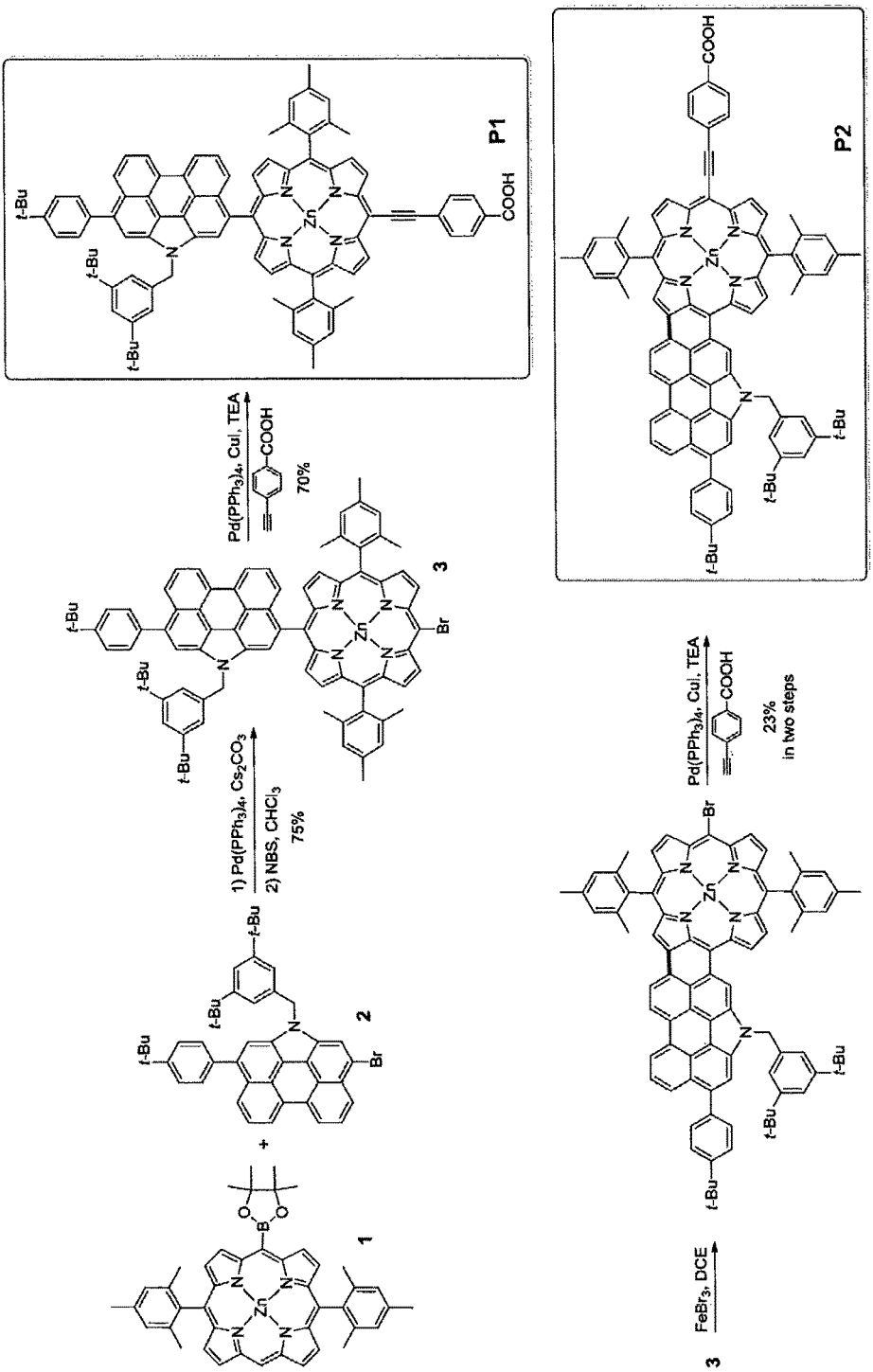
FIG. 1 shows a synthesis scheme for preparing present dye P1 and P2.

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural and chemical changes may be made without departing from the scope of the invention. The various embodiments are not necessarily mutually exclusive, as some embodiments can be combined with one or more other embodiments to form new embodiments.

The key to achieve highly efficient dye-sensitized solar cells (DSSCs) is the design and synthesis of stable organic dyes with appropriate push-pull structure. Moreover, the molecule needs to have broad and intense absorption, and also with appropriate energy levels to complement the electrodes and electrolyte for desired device fabrication.

In one aspect of the invention, there is described a dye-sensitized solar cell comprising a dye molecule. The dye molecule comprises a porphyrin moiety, a perylene moiety, and an anchor group for attachment to a substrate, which are coupled together via linkers. In particular, the perylene moiety is coupled to a first site of the porphyrin moiety via a first linker and the anchor group is coupled to a second site of the porphyrin moiety via a second linker.

Herein disclosed organic dye molecules meet the above requirements due to the following considerations:

Electron-donating groups result in a more red-shifted NIR absorption due to the enhanced intramolecular charge transfer and is also beneficial to a fast electron injection. In present case, the perylene moiety is considered to be a particularly useful building block in organic electronics due to their high photostability and strong absorption ability.

The term "porphyrin" refers to a cyclic structure typically composed of four pyrrole rings together with four nitrogen atoms and two replaceable hydrogens for which various metal atoms can readily be substituted.

The anchor group (such as, but not limited to aromatic carboxylic acid group) serves as a tight binding point for attaching the dye molecule to the semiconductor layer in DSSCs (such as $TiO_2$ layer) and helps to stabilize the low band gap if-system of dyes.

Introduction of an ethynylene group, for example, as a linker into the meso-position of the porphyrin moiety would decrease HOMO-LUMO gap and improve the charge separation in DSSCs.

Certain bulky substituents on the porphyrin moiety or perylene moiety, such as but not limited to 3,5-di-tert-butylphenyl, 2,4,6-trimethylphenyl as well as ortho-alkoxy substituted phenyl groups, were chosen to surmount the solubility problem and reduce dye aggregation in DSSCs.

Accordingly, the dye molecule has the general Formula (I) as shown below:

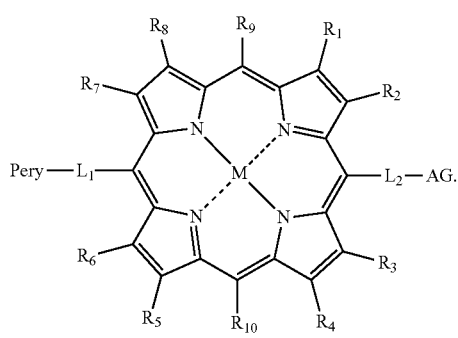

(I)

In Formula (I), M is a metal. In other words, the porphyrin moiety is commonly termed a metalloporphyrin. In preferred embodiments, M is zinc or cobalt. Alternatively, M may be, but not limited to, nickel, iron, and copper.

In Formula (I), AG is an anchor group for attachment to a substrate. The substrate may be a solid material (which may be flexible or rigid) suitable for the attachment of one or more dye molecules. Substrates can be formed of materials including, but not limited to glass, organic polymers, plastic, silicon, minerals (e.g. quartz), semiconducting materials, ceramics, metals, etc. The substrate may be in any suitable shape, including spherical, flat, planar, curved, rod-shaped, etc. In various embodiments, the substrate comprises a semiconducting material particle (including nanoparticle and microparticle), such as titanium dioxide ($TiO_2$) attached to the AG. The attachment may be a chemical or physical bond. For example, the attachment may be a covalent bond.

In preferred embodiments, AG may comprise a phenolic derivative of benzoic acid. For example, AG may be:

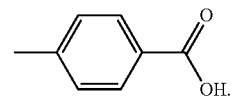

In various embodiments, in Formula (I), each of $R_1$, $R_2$, $R_3$, $R_4$, $R_5$, $R_6$, $R_7$, $R_8$ may be independently selected from the group consisting of hydrogen, halogen, $C_{1-30}$ alkyl, and $C_6$-$C_{20}$ aryl.

In Formula (I), each of $R_1$, $R_2$, $R_3$, $R_4$, $R_5$, $R_6$, $R_7$, $R_8$ may be hydrogen.

In Formula (I), each of $L_1$ and $L_2$ is a linker wherein $L_1$ couples (or links) the Pery moiety to the porphyrin moiety and $L_2$ couples (or links) the porphyrin moiety to the AG.

In various embodiments, each of $L_1$ and $L_2$ may be a direct bond.

In other embodiments, each of $L_1$ and $L_2$ may be an ethynylene group (i.e. —C≡C—).

In further embodiments, $L_1$ may be a direct bond and $L_2$ may be an ethynylene group.

In yet further embodiments, $L_1$ may be an ethynylene group and $L_2$ may be a direct bond.

In various embodiments, each of $R_9$ and $R_{10}$ may be a phenyl (i.e. —$C_6H_5$). The phenyl may be substituted or unsubstituted. For example, $R_9$ may be a mono-, di-, tri-, tetra-, or penta-substituted phenyl. In another example, $R_{10}$ may be a mono-, di-, tri-, tetra-, or penta-substituted phenyl. In further examples, $R_9$, $R_{10}$ or both $R_9$ and $R_{10}$ may be unsubstituted phenyl.

In alternative embodiments, each of $R_9$ and $R_{10}$ may be a benzyl (i.e. —$CH_2C_6H_5$). The benzyl may be substituted or unsubstituted. For example, $R_9$ may be a mono-, di-, tri-, tetra-, or penta-substituted benzyl. In another example, $R_{10}$ may be a mono-, di-, tri-, tetra-, or penta-substituted benzyl. In further examples, $R_9$, $R_{10}$ or both $R_9$ and $R_{10}$ may be unsubstituted benzyl.

In further embodiments, $R_9$ may be a phenyl and $R_{10}$ may be a benzyl. The phenyl or benzyl may be unsubstituted or substituted as defined herein.

In yet further embodiments, $R_9$ may be a benzyl and $R_{10}$ may be a phenyl. The phenyl or benzyl may be unsubstituted or substituted as defined herein.

In various embodiments, $R_9$, or $R_{10}$, or both $R_9$ and $R_{10}$ are independently $C_{1-10}$ alkyl-substituted phenyl.

The term "alkyl", alone or in combination, refers to a fully saturated aliphatic hydrocarbon. In certain embodiments, alkyls are optionally substituted. In certain embodiments, an alkyl comprises 1 to 30 carbon atoms, for example 1 to 10 carbon atoms, wherein (whenever it appears herein in any of the definitions given below) a numerical range, such as "1 to 30" or "$C_{1-30}$", refers to each integer in the given range, e.g. "$C_{1-30}$ alkyl" means that an alkyl group comprising only 1 carbon atom, 2 carbon atoms, 3 carbon atoms, etc., up to and including 30 carbon atoms. Examples of alkyl groups include, but are not limited to, methyl, ethyl, n-propyl, isopropyl, n-butyl, isobutyl, sec-butyl, tert-butyl, pentyl, hexyl, heptyl, octyl and the like.

The term "aryl" refers to an aromatic ring wherein each of the atoms forming the ring is a carbon atom. Aryl rings may be formed by five, six, seven, eight, nine, or more than nine carbon atoms. Aryl groups may be optionally substituted. In various embodiments, any one (or more) of $R_1$, $R_2$, $R_3$, $R_4$, $R_5$, $R_6$, $R_7$, $R_8$ may be a substituted or unsubstituted $C_6$-$C_{20}$ aryl.

A "halo" or "halogen" group refers to fluorine, chlorine, bromine or iodine.

In preferred embodiments, $R_9$, or $R_{10}$, or both $R_9$ and $R_{10}$ are independently methylphenyl (i.e. mono-substituted). The methyl may be ortho-, meta-, or para-substituted on the phenyl.

In certain preferred embodiments, $R_9$, or $R_{10}$, or both $R_9$ and $R_{10}$ are independently trimethylphenyl (i.e. tri-substituted). For example, $R_9$, or $R_{10}$, or both $R_9$ and $R_{10}$ may be 2,4,6-trimethyl phenyl.

In other embodiments, $R_9$, or $R_{10}$, or both $R_9$ and $R_{10}$ are independently $C_{1-15}$ alkoxy-substituted phenyl.

The term "alkoxy", alone or in combination, refers to an aliphatic hydrocarbon having an alkyl-O— moiety. In certain embodiments, alkoxy groups are optionally substituted. $C_{1-15}$ alkoxy therefore refers to an aliphatic hydrocarbon having an alkyl-O— moiety, wherein the alkyl comprises 1 to 15 carbon atoms, for example 1 carbon atom, 2 carbon atoms, 3 carbon atoms, etc., up to and including 15 carbon atoms. Examples of alkoxy groups include, but are not limited to, methoxy, ethoxy, propoxy, butoxy and the like.

In preferred embodiments, $R_9$, or $R_{10}$, or both $R_9$ and $R_{10}$ are independently octyloxyphenyl (i.e. mono-substituted). The octyloxy may be ortho-, meta-, or para-substituted on the phenyl.

In certain preferred embodiments, $R_9$, or $R_{10}$, or both $R_9$ and $R_{10}$ are independently di-octyloxyphenyl (i.e. di-substituted). For example, $R_9$, or $R_{10}$, or both $R_9$ and $R_{10}$ may be 2,6-di-octyloxyphenyl.

In yet further preferred embodiments, $R_9$, or $R_{10}$, or both $R_9$ and $R_{10}$ are independently dodecyloxyphenyl (i.e. mono-substituted). The dodecyloxy may be ortho-, meta-, or para-substituted on the phenyl.

In certain preferred embodiments, $R_9$, or $R_{10}$, or both $R_9$ and $R_{10}$ are independently di-dodecyloxyphenyl (i.e. di-substituted). For example, $R_9$, or $R_{10}$, or both $R_9$ and $R_{10}$ may be 2,6-di-dodecyloxyphenyl.

In Formula (I), Pery is a perylene-based moiety of Formula (II):

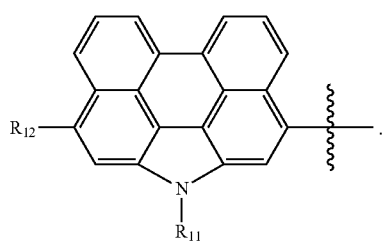

(II)

In Formula (II), each of $R_{11}$ and $R_{12}$ may be independently a substituted or unsubstituted phenyl, or a substituted or unsubstituted benzyl.

In various embodiments, $R_{11}$ may be a benzyl and $R_{12}$ may be a phenyl.

In various embodiments, $R_{12}$ may be a mono-, di-, tri-, tetra, or penta-substituted phenyl.

In preferred embodiments, $R_{12}$ is a $C_{1-10}$ alkyl-substituted phenyl.

In certain embodiments, $R_{12}$ is tert-butylphenyl.

In one preferred embodiment, $R_{12}$ is para-tert-butylphenyl.

In various embodiments, $R_{11}$ may be a mono-, di-, tri-, tetra, or penta-substituted benzyl.

In preferred embodiments, $R_{11}$ is a $C_{1-10}$ alkyl-substituted benzyl.

In yet certain embodiments, $R_{11}$ is a di-$C_{1-10}$ alkyl-substituted benzyl.

In one embodiment, $R_{11}$ is 3,5-di-tert-buytlbenzyl.

In other embodiments, $R_{11}$ may be a phenyl and $R_{12}$ may be a benzyl.

In yet further embodiments, both $R_{11}$ and $R_{12}$ may be phenyl or both $R_{11}$ and $R_{12}$ may be benzyl.

In various preferred embodiments, the dye molecule has any one of the following chemical representations:

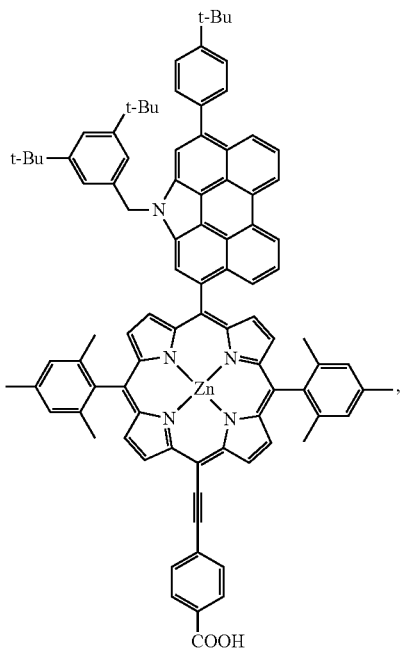

P1

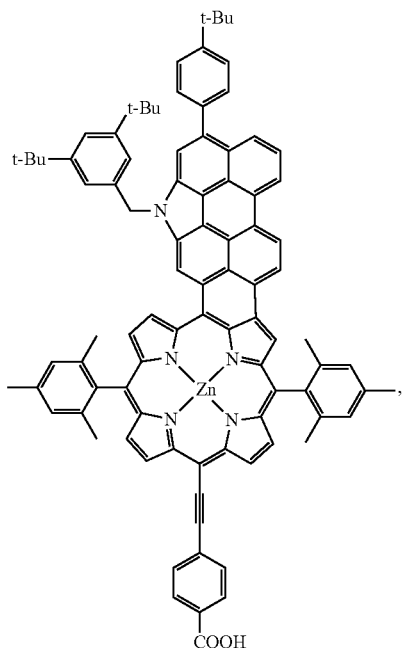

P2

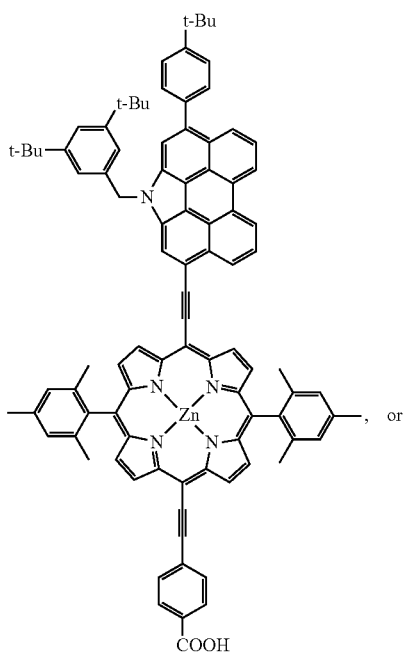

P3

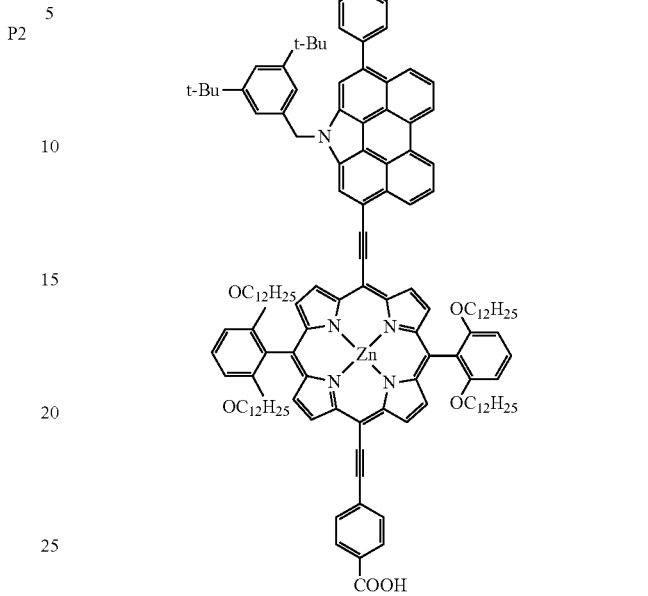

P4

In order that the invention may be readily understood and put into practical effect, particular embodiments will now be described by way of the following non-limiting examples.

EXAMPLES

A series of perylene functionalized porphyrin dyes has been synthesized and employed in dye-sensitized solar cells (DSSCs). More than 11% efficiency has been achieved with the present synthetic dye molecules. The demonstrated DSSC performance is within top 5% as reported. The dyes showed broad absorption with one set at 800 nm. The HOMO and LUOMO orbitals are well separated. The dyes are stable and avoid dye-aggregation on device.

FIG. 1 shows a synthesis scheme for preparing present dye P1 and P2.

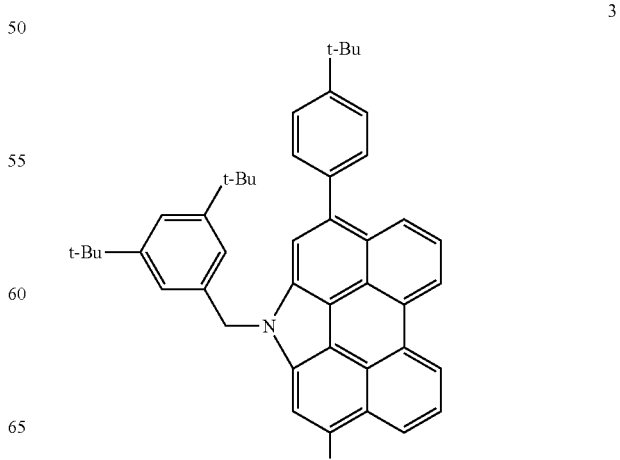

3

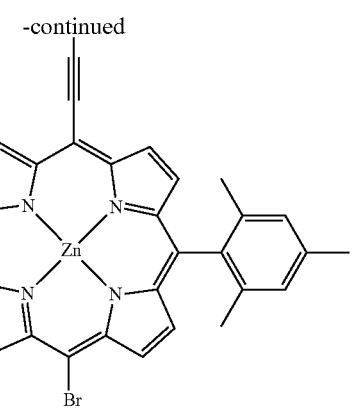

Porphyrin 1 (295 mg, 0.4 mmol), perylene 2 (271.5 mg, 0.4 mmol), Pd(PPh$_3$)$_4$ (46 mg, 0.04 mmol), and Cs$_2$CO$_3$ (260 mg, 0.8 mmol) were dried under vacuum and then purged with argon. To this were added degassed toluene (10 mL) and DMF (5 mL), and the mixture was stirred at 96° C. for 36 h. After cooling, water was added and the product was extracted with ethyl acetate (3×30 mL). The organic layer was washed with saturated brine and dried over anhydrous Na$_2$SO$_4$. The solvent was removed under vacuum, and the residue was purified by column chromatography (silica gel, DCM/hexane=1:3) to give a purple solid as the coupling product 3a (362 mg), which was subjected to the subsequent bromination reaction. To a CHCl$_3$ (100 mL) and pyridine (3 mL) solution of 3a was added a CHCl$_3$ solution (50 mL) of N-bromosuccinimide (NBS) (56 mg, 0.32 mmol) dropwise in 10 min at 0° C. Acetone (100 mL) was added to the reaction mixture, and the resulting solution was concentrated and chromatographed on a short slica gel with CHCl$_3$ as an eluent to allow isolation of brominated compound 3 (386 mg, 75% yield for two steps). Characterization for 3a: $^1$H NMR (CDCl$_3$, 400 MHz) δ 10.21 (s, 1H), 9.37 (d, J=4.5 Hz, 2H), 8.93 (d, J=4.4 Hz, 2H), 8.77 (m, 3H), 8.69 (m, 3H), 8.54 (s, 1H), 8.30 (d, J=8.4 Hz, 1H), 7.88 (dd, J=15.1, 6.9 Hz, 2H), 7.73 (d, J=8.1 Hz, 2H), 7.63 (d, J=8.2 Hz, 2H), 7.46 (m, 1H), 7.30-7.21 (m, 8H), 5.98 (s, 2H), 2.63 (s, 6H), 1.89 (s, 6H), 1.83 (s, 6H), 1.49 (s, 9H), 1.12 (s, 18H). $^{13}$C NMR (100 MHz, CHCl$_3$) δ151.37, 151.10, 150.07, 149.99, 149.91, 149.69, 139.29, 139.08, 138.92, 138.02, 137.43, 137.06, 136.59, 133.56, 132.61, 132.53, 132.37, 132.06, 131.31, 131.21, 130.83, 130.39, 129.99, 128.20, 127.68, 127.61, 126.57, 125.35, 125.15, 124.77, 124.41, 123.47, 121.94, 121.68, 121.23, 120.50, 120.28, 118.92, 118.74, 117.98, 117.34, 114.71, 105.41, 50.41, 34.70, 31.53, 31.32, 21.75, 21.62, 21.45. IR (thin film) ν 2961.35 (CH$_3$), 2918.66 (CH$_2$), 2864.69 (CH$_3$), 1600.41 (C=C), 1475.05 (C=N), 1380.19 (C(CH$_3$)$_3$), 1362.47 (C(CH$_3$)$_3$), 1298.29 (CH$_2$), 1058.53 (Ph), 997.35 (Ph), 832.74 (Ph, para), 798.99 (Ph, meta), 757.99 (Ph, meta), 723.42 (Ph, meta) cm$^{-1}$. HRMS (APCI): m/z=1206.5387 (M$^+$+1) calcd. for C$_{83}$H$_{76}$N$_5$Zn: 1206.5399 (error=−1.0 ppm). Characterization for 3: $^1$H NMR (400 MHz, THF) δ 9.65 (d, J=4.5 Hz, 2H), 8.83 (d, J=7.4 Hz, 1H), 8.72 (d, J=4.5 Hz, 4H), 8.63 (d, J=4.5 Hz, 2H), 8.51 (d, J=4.4 Hz, 2H), 8.22 (d, J=8.3 Hz, 1H), 8.05 (s, 1H), 7.82 (t, J=7.9 Hz, 1H), 7.68 (dd, J=25.6, 8.1 Hz, 4H), 7.49-7.24 (m, 8H), 7.13 (d, J=8.3 Hz, 1H), 6.09 (s, 2H), 2.59 (s, 6H), 1.89 (s, 6H), 1.86 (s, 6H), 1.48 (s, 9H), 1.12 (s, 18H). $^{13}$C NMR (100 MHz, THF) δ 152.21, 151.39, 150.60, 150.46, 150.16, 149.65, 139.78, 139.71, 139.29, 138.44, 137.81, 137.70, 137.55, 134.04, 133.47, 133.04, 132.99, 131.86, 131.63, 131.34, 131.16, 130.89, 130.77, 130.32, 128.53, 127.99, 126.50, 125.52, 124.92, 124.78, 124.61, 124.27, 123.83, 122.50, 121.66, 121.51, 120.81, 120.68, 119.53, 118.25, 117.63, 115.18, 103.39, 50.28, 34.82, 31.33, 31.22, 30.15, 21.47, 21.03. IR (thin film) ν 2960.66 (CH$_3$), 2922.78 (CH$_2$), 2852.19 (CH$_3$), 1652.15 (C=C), 1459.10 (C=N), 1362.45 (C(CH$_3$)$_3$), 1298.46 (CH$_2$), 1204.87 (CH$_2$), 1113.98 (CH$_2$), 1079.29 (Ph), 997.50 (Ph), 827.72 (Ph, para), 798.00 (Ph, meta), 758.22 (Ph, meta) cm$^{-1}$. HRMS (APCI): m/z=1284.4492 (M$^+$+1) calcd. for C$_{83}$H$_{75}$BrN$_5$Zn: 1284.4499 (error=−0.5 ppm).

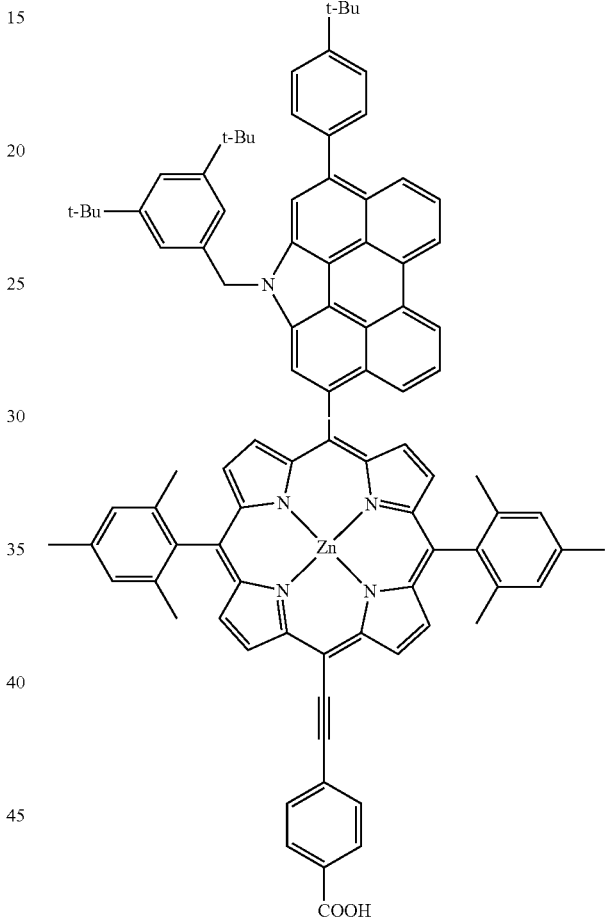

P1

A 50 mL round bottle flask was charged with 3 (64 mg, 0.05 mmol), 4-ethynylbenzoic acid (29.2 mg, 0.2 mmol), Pd(RPh$_3$)$_4$ (6 mg, 0.005 mmol), Et$_3$N (4 mL) and THF (20 mL) under argon. The reaction mixture was stirred at 50° C. for 24 hours. After removal of the solvents, the crude product was purified by column chromatography (silica gel, DCM:MeOH=50:1) to give the purple solid product P1 (48 mg, 70% yield). Characterization for P1: $^1$H NMR (400 MHz, THF) δ 9.78 (d, J=4.5 Hz, 2H), 8.90-8.68 (m, 5H), 8.62 (d, J=4.5 Hz, 2H), 8.48 (d, J=4.5 Hz, 2H), 8.31-8.12 (m, 5H), 8.06 (s, 1H), 7.83 (t, J=7.9 Hz, 1H), 7.69 (dd, J=26.2, 8.1 Hz, 4H), 7.49-7.25 (m, 8H), 7.13 (d, J=8.3 Hz, 1H), 6.11 (s, 2H), 2.60 (s, 6H), 1.92 (s, 6H), 1.90 (s, 6H), 1.49 (s, 9H), 1.14 (s, 18H). $^{13}$C NMR (100 MHz, THF) δ 167.38, 153.21, 152.24, 152.15, 151.35, 150.93, 150.62, 140.49, 140.01, 139.96, 139.19, 138.59, 138.44, 138.27, 134.77, 133.72, 132.38, 132.23, 131.93, 131.64, 131.06, 130.02, 129.28, 128.74, 127.26, 126.28, 125.67, 125.52, 124.57, 123.26, 122.42, 122.27, 121.94, 121.44, 120.91, 119.00, 118.37, 115.94, 98.77, 97.39, 95.97, 51.03, 35.58, 35.32, 32.08, 31.97, 22.21, 21.78. IR (thin film) v 3294.00 (OH), 2960.82 (CH$_3$), 2915.50 (CH$_2$), 2864.11 (CH$_3$), 2185.58 (C≡C), 1690.98 (C=O), 1602.45 (C=C), 1475.08 (CH$_2$), 1436.96 (C=N), 1362.10 (C(CH$_3$)$_3$), 1297.44 (CH$_2$), 1273.74 (Ph), 1205.21 (CH$_2$), 1172.82 (Ph), 994.94 (Ph), 856.28 (Ph, para), 797.23 (Ph, meta), 756.56 (Ph, meta), 717.10 (Ph, meta), 694.58 (Ph, meta), 540.74 (Zn—N) cm$^{-1}$. HRMS (APCI): m/z=1350.5609 (M$^+$+1) calcd. for C$_{92}$H$_{80}$N$_5$O$_2$Zn: 1350.5598 (error=+0.8 ppm).

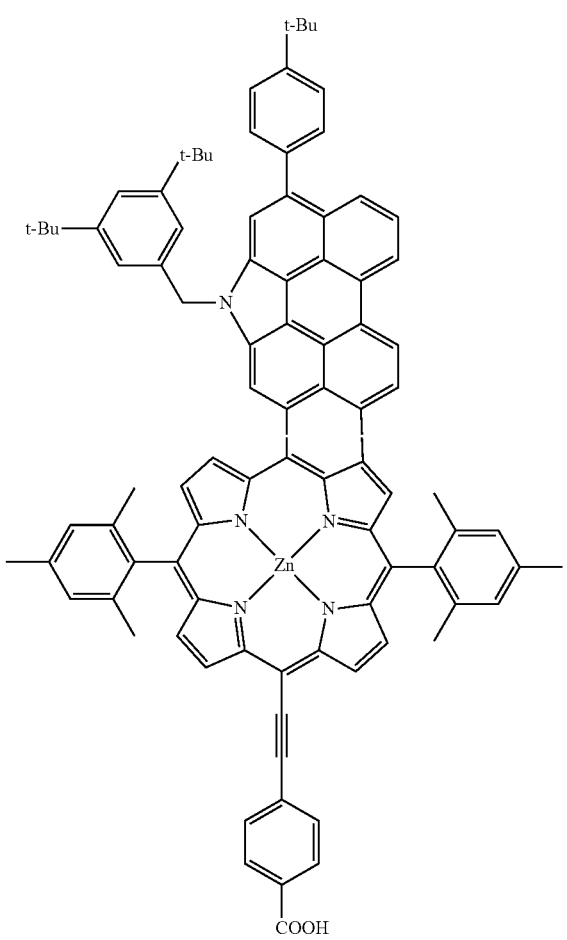

P2

To a solution of 3 (128 mg, 0.1 mmol) in degassed anhydrous dichloroethane (40 mL) was added a FeBr$_3$ (59 mg, 0.2 mmol). The reaction mixture was carried out at room temperature for 24 h and then quenched by addition of a saturated NaHCO$_3$ solution. The organic layer was washed with saturated brine and dried over anhydrous Na$_2$SO$_4$. The solvent was removed under vacuum and the residue was purified by column chromatography (silica gel, DCM: hexane=1:4) to give a brown solid as the ring fused product (37 mg). To this brown solid in a 50 mL round bottle flask was added 4-ethynylbenzoic acid (17 mg, 0.12 mmol), Pd(PPh$_3$)$_4$ (4 mg, 0.003 mmol), Et$_3$N (4 mL) and THF (20 mL) under argon. The reaction mixture was stirred at 50° C. for 24 hours. After removal of the solvents, the crude product was purified by column chromatography (silica gel, DCM:MeOH=50:1) to give the dark brown solid product P2 (31 mg, 23% yield in two steps). Characterization for P2: $^1$H NMR (400 MHz, THF) δ 9.64-9.49 (m, 2H), 9.25 (d, J=14.0 Hz, 2H), 9.12 (br, 1H), 9.04 (s, 1H), 8.77 (s, 1H), 8.57 (dd, J=11.7, 4.4 Hz, 2H), 8.47 (s, 1H), 8.30 (d, J=5.8 Hz, 1H), 8.21 (d, J=7.9 Hz, 2H), 8.16-8.00 (m, 4H), 7.69 (br, 5H), 7.56 (s, 2H), 7.49 (s, 1H), 7.39 (s, 2H), 7.36 (s, 2H), 6.33 (s, 2H), 2.70 (s, 3H), 2.67 (s, 3H), 1.99 (s, 6H), 1.97 (s, 6H), 1.47 (s, 9H), 1.23 (s, 18H). $^{13}$C NMR was not taken due to the compound low solubility. IR (thin film) v 3640.43 (OH), 2955.43 (CH$_3$), 2913.45 (CH$_2$), 2869.65 (CH$_3$), 2187.13 (C≡C), 1719.62 (C=O) 1443.92 (CH$_2$), 1430.93 (C=N), 1360.38 (C(CH$_3$)$_3$), 1311.10 (CH$_2$), 1246.39 (Ph), 1231.02 (Ph), 1213.08 (Ph), 1150.24 (Ph), 862.19 (Ph, para), 774.49 (Ph, meta), 768.67 (Ph, meta) 577.77 (Zn—N) cm$^{-1}$. HRMS (APCI): m/z=1348.5456, (M$^+$+1), calcd. for C$_{92}$H$_{78}$N$_5$O$_2$Zn: 1348.5441 (error=+1.1 ppm).

Figure 2:
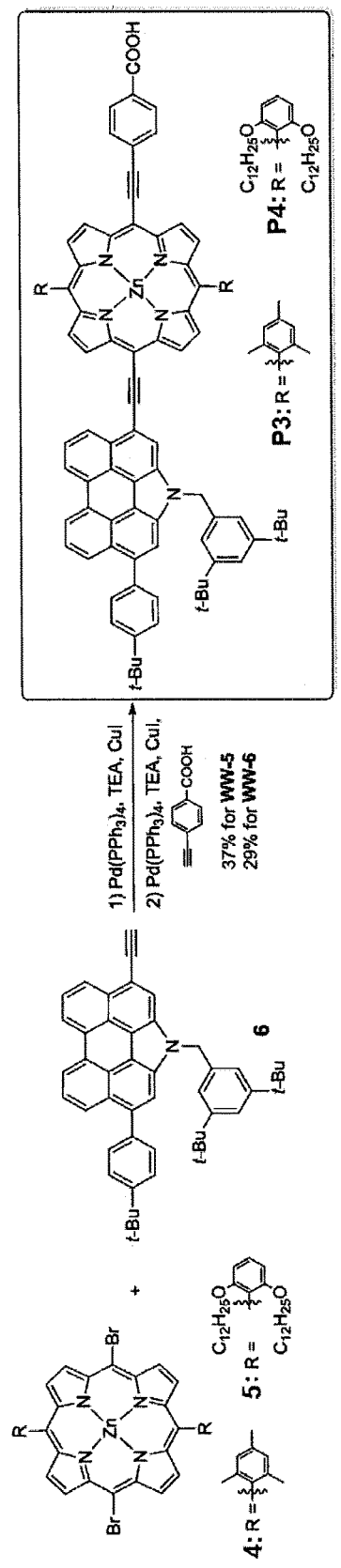
FIG. 2 shows a synthesis scheme for preparing present dye P3 and P4.

FIG. 2 shows a synthesis scheme for preparing present dye P3 and P4.

A 100 mL round bottle flask was charged with dibromo porphyrin 4 (77 mg, 0.1 mmol), ethynyl substituted perypene 6 (63 mg, 0.1 mmol), Pd(PPh$_3$)$_4$ (12 mg, 0.01 mmol), Et$_3$N (8 mL) and THF (40 mL) under argon. The reaction mixture was stirred at 50° C. for 24 hours. After removal of the solvents, the crude product was purified by column chromatography (silica gel, DCM:hexane=1:5) to give the purple solid product (59 mg), which was subjected into the next step of coupling reaction directly. To this purple solid was added 4-ethynylbenzoic acid (26 mg, 0.18 mmol), Pd(PPh$_3$)$_4$ (6 mg, 0.005 mmol), Et$_3$N (4 mL) and THF (20 mL) under argon. The reaction mixture was stirred at 50° C. for 24 hours. After removal of the solvents, the crude product was purified by column chromatography (silica gel, DCM:MeOH=50:1) to give the purple solid product P3 (50 mg, 37% yield in two steps). Characterization for P3: $^1$H NMR (500 MHz, CDCl$_3$) δ 9.91 (d, J=4.4 Hz, 2H), 9.69 (d, J=4.5 Hz, 2H), 9.15 (d, J=8.1 Hz, 1H), 8.92 (d, J=7.6 Hz, 1H), 8.85 (d, J=7.5 Hz, 1H), 8.76-8.67 (m, 4H), 8.24 (d, J=8.0 Hz, 2H), 8.19 (d, J=8.2 Hz, 1H), 8.16-8.09 (m, 3H), 7.89 (s, 1H), 7.86-7.79 (m, 1H), 7.63 (q, J=8.4 Hz, 4H), 7.49 (d, J=1.7 Hz, 2H), 7.43 (s, 1H), 7.36 (s, 5H), 6.15 (s, 2H), 2.66 (s, 6H), 1.93 (s, 12H), 1.46 (s, 9H), 1.27 (s, 18H). $^{13}$C NMR (125 MHz, THF) δ 167.43, 153.20, 152.92, 152.36, 151.05, 150.89, 150.81, 140.23, 140.18, 140.03, 139.99, 138.61, 138.37, 136.39, 134.99, 133.04, 132.42, 132.21, 132.05, 131.96, 131.76, 131.66, 131.26, 131.07, 130.96, 129.75, 129.25, 128.83, 126.62, 126.28, 125.97, 125.83, 125.79, 125.59, 125.33, 123.20, 122.63, 122.50, 121.98, 119.66, 119.46, 118.45, 117.98, 115.77, 103.21, 100.20, 98.96, 98.47, 97.95, 97.00, 96.46, 51.08, 35.70, 34.37, 32.00, 30.83, 22.12, 21.79. IR (thin film) ν 3437.78 (OH), 2952.21 (CH$_3$), 2917.72 (CH$_2$), 2849.90 (CH$_3$), 2176.56 (C≡C), 1638.48 (C=O), 1602.41 (C=C), 1475.01 (C=N), 1296.05 (CH$_2$), 1264.32 (Ph), 1059.48 (Ph), 997.98 (Ph), 853.25 (Ph, para), 795.93 (Ph, meta), 757.25 (Ph, meta), 713.89 (Ph, meta) cm$^{-1}$. HRMS (APCI): m/z=1374.5630, (M$^+$+1) calcd. for C$_{94}$H$_{80}$N$_5$O$_2$Zn: 1374.5598 (error=+2.3 ppm).

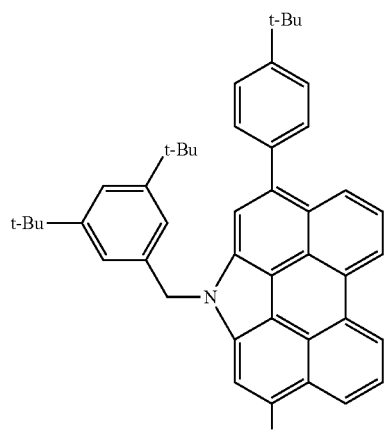

P4

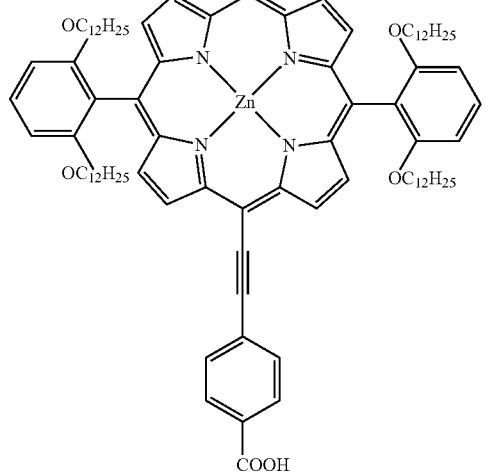

A 100 mL round bottle flask was charged with dibromo porphyrin 5 (142 mg, 0.1 mmol), ethynyl substituted perypene 6 (63 mg, 0.1 mmol), Pd(PPh$_3$)$_4$ (12 mg, 0.01 mmol), Et$_3$N (8 mL) and THF (40 mL) under argon. The reaction mixture was stirred at 50° C. for 24 hours. After removal of the solvents, the crude product was purified by column chromatography (silica gel, DCM:hexane=1:8) to give the purple solid product (74 mg), which was subjected into the next step of coupling reaction directly. To this purple solid was added 4-ethynylbenzoic acid (22 mg, 0.15 mmol), Pd(PPh$_3$)$_4$ (5 mg, 0.004 mmol), Et$_3$N (4 mL) and THF (20 mL) under argon. The reaction mixture was stirred at 50° C. for 24 hours. After removal of the solvents, the crude product was purified by column chromatography (silica gel, DCM:MeOH=50:1) to give the purple solid product P4 (59 mg, 29% yield in two steps). Characterization for P4: $^1$H NMR (400 MHz, CDCl$_3$) δ 9.87 (d, J=4.4 Hz, 2H), 9.62 (d, J=4.4 Hz, 2H), 9.23 (d, J=8.1 Hz, 1H), 8.92 (d, J=7.6 Hz, 1H), 8.85-8.79 (m, 4H), 8.73 (s, 1H), 8.17 (ddd, J=24.9, 18.3, 8.0 Hz, 7H), 7.87 (s, 1H), 7.83 (d, J=8.0 Hz, 1H), 7.73 (t, J=8.4 Hz, 2H), 7.64 (t, J=5.9 Hz, 4H), 7.52 (s, 2H), 7.45 (s, 1H), 7.10 (d, J=8.5 Hz, 4H), 6.16 (s, 2H), 3.92 (t, J=6.4 Hz, 8H), 1.46 (s, 9H), 1.30 (s, 18H), 1.05-0.68 (m, 92H). $^{13}$C NMR was not taken due to its low signal. IR (thin film) ν 3436.80 (OH), 2923.01 (CH$_2$), 2851.73 (CH$_3$), 2186.01 (C≡C), 1689.64 (C=O), 1602.96 (C=C), 1455.93 (C=N), 1296.02 (CH$_2$), 1247.74 (Ph), 1207.19 (CH$_2$), 1100.20 (Ph), 1061.63 (Ph), 998.11 (Ph), 793.36 (Ph, para), 757.34 (Ph, meta), 723.11 ((CH$_2$), n>7), 711.28 (Ph, meta) cm$^{-1}$. HRMS (APCI): m/z=2027.1949, (M$^+$+1) calcd. for C$_{136}$H$_{164}$N$_5$O$_6$Zn: 2027.1968 (error=-0.9 ppm).

Figure 3:
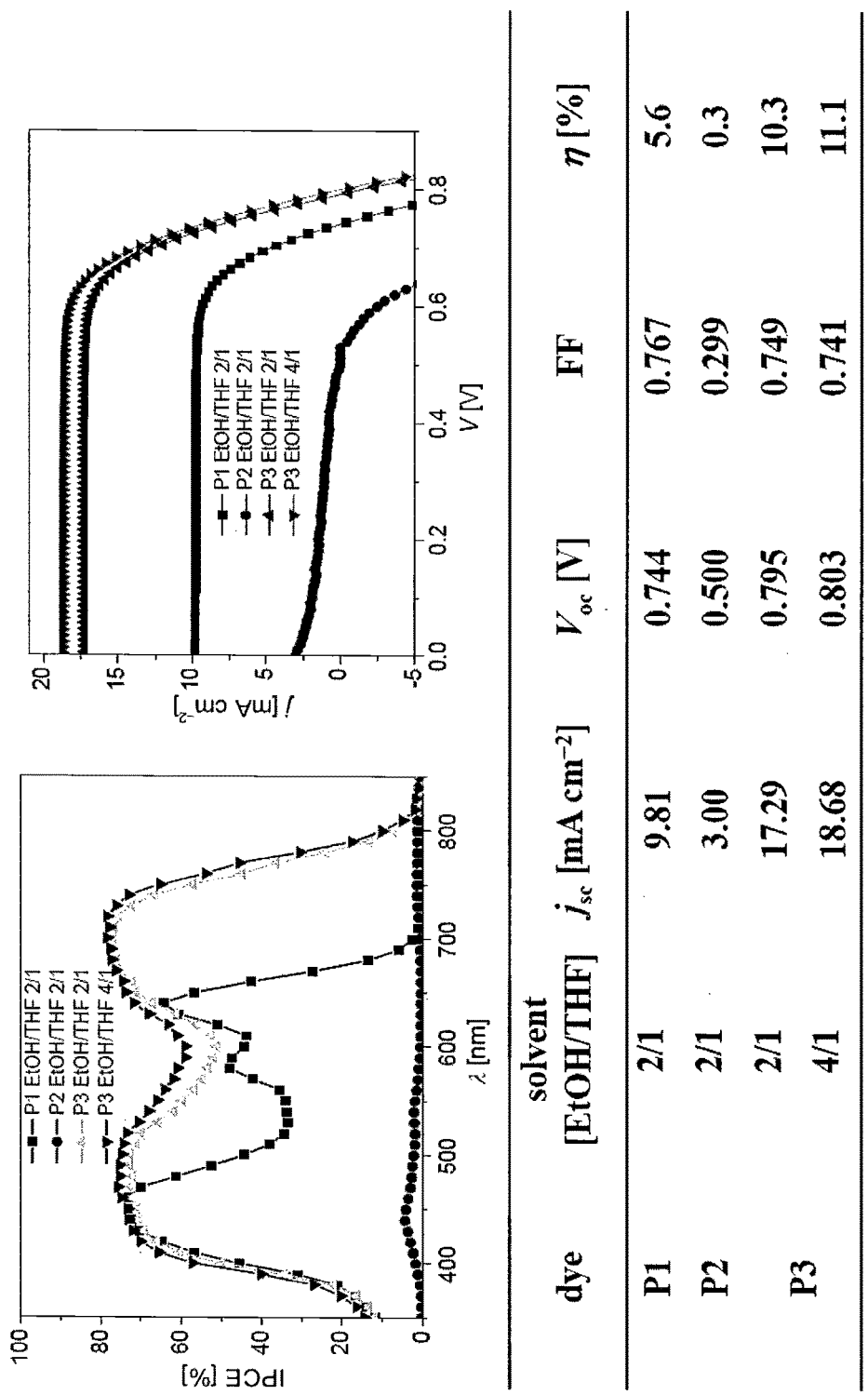
FIG. 3 shows device performance for various dyes P1, P2, and P3.

FIG. 3 shows device performance for various dyes P1, P2, and P3.

A 2.1-μm-thick, transparent layer of 22-nm-sized TiO$_2$ particles was first screen-printed on FTO glass (Nippon Sheet Glass, Solar, 4 mm thick) and further coated with a 5.0-μm-thick second layer of scattering titania particles (WER4-O, Dyesol) to produce a bilayer titania film, which was used later as the negative electrode of a DSSC. The preparation procedures of TiO$_2$ nanocrystals and paste for screen-printing were reported in a previous paper (Wang, P.; Zakeeruddin, S. M.; Comte, P.; Charvet, R.; Humphry- Baker, R.; Gratzel, M. *J. Phys. Chem. B* 2003, 107, 14336). The film thickness was monitored with a bench-top Annbios XP-1 stylus profilometer. After sintering at 500° C. and cooling to 80° C., a circular titania electrode (~0.28 cm²) was stained by immersing it overnight into a solution of 150 μM dye dissolved in a binary solvent of tetrahydrofuran and ethanol (volume ratio, 1/4). The dye-coated titania electrode was then rinsed with acetonitrile and dried by air flow, and was further assembled with a thermally platinized FTO positive electrode by a 25-μm-thick Surlyn (DuPont) hot-melt gasket and sealed up by heating. The internal space was perfused with an electrolyte with the aid of a vacuum-back-filling system. Present cobalt electrolyte is composed of 0.25 M tris(2,2'-bipyridine)cobalt(II) di[bis(trifluoromethanesulfonyl)imide], 0.05 M tris(2,2'-bipyridine)cobalt(III) tris[bis(trifluoromethanesulfonyl)imide], 0.5 M TBP and 0.1 M LiTFSI in acetonitrile.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A dye-sensitized solar cell comprising a dye molecule of Formula (I):

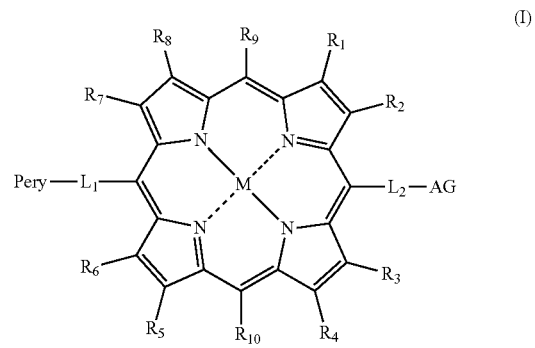

wherein:
M is zinc, cobalt, nickel, iron, or copper;
each of $L_1$ and $L_2$ is a linker and is independently selected from the group consisting of a direct bond and an ethynylene group;
each of $R_1$, $R_2$, $R_3$, $R_4$, $R_5$, $R_6$, $R_7$, $R_8$ is independently selected from the group consisting of hydrogen, halogen, $C_{1-30}$ alkyl, and $C_6-C_{20}$ aryl;
each of $R_9$ and $R_{10}$ is independently a substituted or unsubstituted phenyl, or a substituted or unsubstituted benzyl;
AG is an anchor group for attachment to a substrate; and
Pery is a perylene-based moiety of Formula (II):

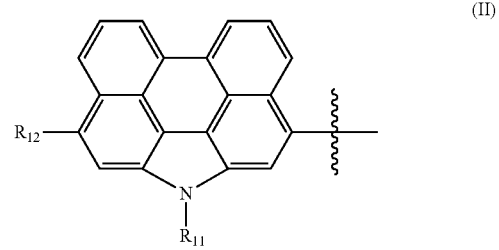

wherein:
each of $R_{11}$ and $R_{12}$ is independently a substituted or unsubstituted phenyl, or a substituted or unsubstituted benzyl.

2. The dye-sensitized solar cell of claim 1, wherein $R_{11}$ is a substituted or unsubstituted benzyl and $R_{12}$ is a substituted or unsubstituted phenyl.

3. The dye-sensitized solar cell of claim 2, wherein $R_{12}$ is a mono-, di-, tri-, tetra-, or penta-substituted phenyl.

4. The dye-sensitized solar cell of claim 2, wherein $R_{12}$ is a $C_{1-10}$ alkyl-substituted phenyl.

5. The dye-sensitized solar cell of claim 4, wherein $R_{12}$ is tert-butylphenyl.

6. The dye-sensitized solar cell of claim 5, wherein $R_{12}$ is para-tert-butylphenyl.

7. The dye-sensitized solar cell of claim 2, wherein $R_{11}$ is a mono-, di-, tri-, tetra-, or penta-substituted benzyl.

8. The dye-sensitized solar cell of claim 7, wherein $R_{11}$ is a $C_{1-10}$ alkyl-substituted benzyl.

9. The dye-sensitized solar cell of claim 8, wherein $R_{11}$ is a di-$C_{1-10}$ alkyl-substituted benzyl.

10. The dye-sensitized solar cell of claim 9, wherein $R_{11}$ is 3,5-di-tert-butylbenzyl.

11. The dye-sensitized solar cell of claim 1, wherein $R_9$, or $R_{10}$, or both $R_9$ and $R_{10}$ are substituted or unsubstituted phenyl.

12. The dye-sensitized solar cell of claim 11, wherein each of $R_9$ and $R_{10}$ is independently a mono-, di-, tri-, tetra-, or penta-substituted phenyl.

13. The dye-sensitized solar cell of claim 12, wherein $R_9$, or $R_{10}$, or both $R_9$ and $R_{10}$ are independently $C_{1-10}$ alkyl-substituted phenyl.

14. The dye-sensitized solar cell of claim 13, wherein $R_9$, or $R_{10}$, or both $R_9$ and $R_{10}$ are methylphenyl.

15. The dye-sensitized solar cell of claim 14, wherein $R_9$, or $R_{10}$, or both $R_9$ and $R_{10}$ are trimethylphenyl.

16. The dye-sensitized solar cell of claim 15, wherein $R_9$, or $R_{10}$, or both $R_9$ and $R_{10}$ are 2,4,6-trimethylphenyl.

17. The dye-sensitized solar cell of claim 12, wherein $R_9$, or $R_{10}$, or both $R_9$ and $R_{10}$ are independently a $C_{1-15}$ alkoxy-substituted phenyl.

18. The dye-sensitized solar cell of claim 17, wherein $R_9$, or $R_{10}$, or both $R_9$ and $R_{10}$ are octyloxyphenyl.

19. The dye-sensitized solar cell of claim 18, wherein $R_9$, or $R_{10}$, or both $R_9$ and $R_{10}$ are 2,6-di-octyloxyphenyl.

20. The dye-sensitized solar cell of claim 17, wherein $R_9$, or $R_{10}$, or both $R_9$ and $R_{10}$ are dodecyloxyphenyl.

21. The dye-sensitized solar cell of claim 20, wherein $R_9$, or $R_{10}$, or both $R_9$ and $R_{10}$ are 2,6-di-dodecyloxyphenyl.

22. The dye-sensitized solar cell of claim 1, wherein AG comprises a phenolic derivative of benzoic acid.

23. A dye molecule of Formula (I):

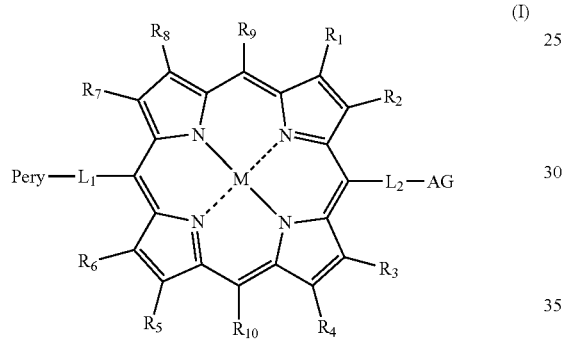

(I)

wherein:

M is zinc, cobalt, nickel, iron, or copper;

each of $L_1$ and $L_2$ is a linker and is independently selected from the group consisting of a direct bond and an ethynylene group;

each of $R_1$, $R_2$, $R_3$, $R_4$, $R_5$, $R_6$, $R_7$, $R_8$ is independently selected from the group consisting of hydrogen, halogen, $C_{1-30}$ alkyl, and $C_6$-$C_{20}$ aryl;

each of $R_9$ and $R_{10}$ is independently a substituted or unsubstituted phenyl, or a substituted or unsubstituted benzyl;

AG is an anchor group for attachment to a substrate; and

Pery is a perylene-based moiety of Formula (II):

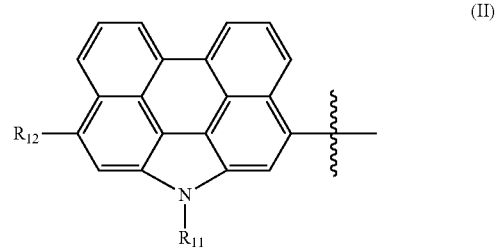

(II)

wherein:

each of $R_{11}$ and $R_{12}$ is independently a substituted or unsubstituted phenyl, or a substituted or unsubstituted benzyl.

* * * * *